United States Patent [19]

Kelly

[11] Patent Number: 4,637,897
[45] Date of Patent: Jan. 20, 1987

[54] NEMATIC COMPOUNDS

[75] Inventor: Stephen M. Kelly, Oberrohrdorf, Switzerland

[73] Assignee: Merck Patent Gesellschaft mit beschränkter Haftung, Darmstadt, Fed. Rep. of Germany

[21] Appl. No.: 638,089

[22] Filed: Aug. 6, 1984

[30] Foreign Application Priority Data

Aug. 4, 1983 [CH] Switzerland ............... 234/83
Mar. 23, 1984 [DE] Fed. Rep. of Germany ....... 3410734

[51] Int. Cl.$^4$ .............. C07C 49/84; C07C 43/225; C07C 39/42; C07C 69/75; C07C 25/13; C07C 121/52; C07C 121/56; C09K 19/30
[52] U.S. Cl. ............... 252/299.63; 558/415; 558/414; 558/423; 558/411; 252/299.5; 350/350 R; 350/350 S; 560/65; 560/73; 560/126; 560/1; 560/8; 568/631; 568/647; 570/129; 570/182
[58] Field of Search ............. 252/299.63, 299.5; 350/350 R, 350 S; 560/1, 126, 65, 73, 8; 260/465 D, 465 F, 465 R, 465 C; 568/647, 631; 570/129, 182

[56] References Cited

U.S. PATENT DOCUMENTS

| | | | |
|---|---|---|---|
| 4,357,078 | 11/1982 | Carr et al. | 252/299.63 |
| 4,368,135 | 1/1983 | Osman et al. | 252/299.63 |
| 4,393,258 | 7/1983 | Sato et al. | 252/299.63 |
| 4,400,061 | 8/1983 | Carr et al. | 252/299.62 |
| 4,400,293 | 8/1983 | Romer et al. | 252/299.5 |
| 4,439,015 | 2/1984 | Rich et al. | 252/299.63 |
| 4,479,885 | 10/1984 | Mukoh et al. | 252/299.63 |
| 4,480,117 | 10/1984 | Takatsu et al. | 252/299.63 |
| 4,512,636 | 4/1985 | Andrews et al. | 252/299.61 |
| 4,514,317 | 4/1985 | Tuonl et al. | 252/299.62 |

FOREIGN PATENT DOCUMENTS

| | | | |
|---|---|---|---|
| 58512 | 8/1982 | European Pat. Off. | 252/299.63 |
| 84194 | 7/1983 | European Pat. Off. | 252/299.61 |
| 103681 | 3/1984 | European Pat. Off. | 252/299.63 |
| 107116 | 5/1984 | European Pat. Off. | 252/299.63 |
| 3237367 | 4/1983 | Fed. Rep. of Germany | 252/299.63 |
| 3335550 | 4/1984 | Fed. Rep. of Germany | 252/299.63 |
| 3317597 | 11/1984 | Fed. Rep. of Germany | 252/299.63 |
| 2134110 | 8/1984 | United Kingdom | 252/299.63 |

OTHER PUBLICATIONS

Osman, M. A., et al., Mol. Cryst. Liq. Cryst., vol. 82 (Letters), pp. 339–344 (1983).

*Primary Examiner*—Teddy S. Gron
*Attorney, Agent, or Firm*—Millen & White

[57] ABSTRACT

Nematic compounds with a negative DC antisotropy, characterized by the formula I

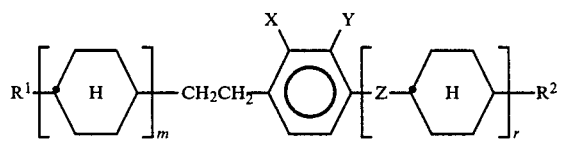

in which m=1 or 2, r is zero or 1 and m+r=1 or 2, and $R^1$ and $R^2$ are identical or different and are selected from alkyl and alkoxy groups each having 1–12 carbon atoms in a straight or branched chain, which may be chiral, Z is a bridge member selected from a single bond and the groups of the formulae —CH$_2$CH$_2$—, —OCH$_2$—, —O—CO— or —CO—O—, one of the groups X and Y is selected from fluorine, chlorine, bromine and cyano and the other of the groups X and Y is selected from hydrogen, fluorine, chlorine, bromine and cyano, with the proviso that m=r=1 if X and Y are both cyano, are suitable as components for liquid crystal mixtures having an overall negative DC anisotropy, such as are required in particular for electro-optical displays of the type of guest/host displays or homotropic-nematic displays.

19 Claims, No Drawings

NEMATIC COMPOUNDS

BACKGROUND OF THE INVENTION

This invention relates to novel nematic compounds which have a negative anisotropy of the dielectric constant (DC) and are suitable as components for liquid crystal (LC) mixtures. This invention also relates to nematic LC mixtures which contain the novel compounds as components and have an overall negative DC anisotropy.

Nematic liquid crystal mixtures with negative dielectric constant anisotropy (DCA) are required for operating certain displays, for example for the so-called guest-/host displays (GHD) and homotropic-nematic displays (HND) with a positive image display or positive contrast. Similar compounds are known, for example from J. C. Dubois et al., Mol. Cryst. Liq. Cryst. 42 [1977] 139; German Offenlegungschriften No. 2,240,864, 2,613,293, 2,835,682, and 2,937,700, Soviet Patent Specification No. 562,547 and European patent application No. 80200464.8).

However, no satisfactory nematic LC mixtures, which have a sufficiently strong negative DCA (for example 2 or better) in combination with the further properties, necessary for perfect operation of display cells, of LC mixtures, such as chemical stability in general, photochemical, electrochemical and thermal stability, and a sufficiently wide range of anisotropy as well as sufficiently short response times even at low temperatures, for example at most about one second at the lower end of the anisotropy range, are yet obtainable by means of the compounds hitherto known.

SUMMARY OF THE INVENTION

Thus, it is an object of the invention to provide novel nematic compounds which enable LC mixtures with a markedly negative DCA and the further properties mentioned to be prepared.

These objects have been obtained by providing compounds of the formula I

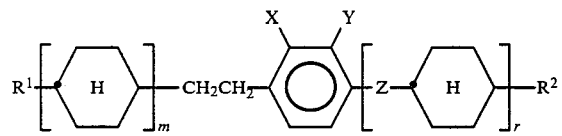

in which m=1 or 2, r is zero or 1 and m+r=1 or 2, and $R^1$ and $R^2$ are identical or different and are selected from alkyl and alkoxy groups each having 1-12 carbon atoms in a straight or branched chain, which may be chiral, Z is a bridge member selected from a single bond and the groups of the formulae —CH$_2$CH$_2$—, —OCH$_2$—, —O—CO— or —CO—O—, one of the groups X and Y is selected from fluorine, chlorine, bromine and cyano and the other of the groups X and Y is selected from hydrogen, fluorine, chlorine, bromine and cyano, with the proviso that m=r=1 if X and Y are both cyano.

It has been found that the compounds of the formula I are outstandingly suitable as components of liquid-crystalline phases. In particular, stable liquid-crystalline phases with an overall negative dielectric anisotropy and comparatively low viscosity can be prepared by means of these compounds.

The compounds of the formula I can be used, in the same way as similar compounds, as components of liquid-crystalline phases, such as are required especially for electro-optical displays of the type of guest/host displays or homotropic-nematic displays.

Moreover, by the provision of the compounds of the formula (I), the range of liquid-crystalline substances, which are suitable under different application aspects for the preparation of nematic mixtures, is quite generally widened considerably.

The subject of the invention thus concerns the compounds of the formula (I) and the use of the compounds of the formula (I) as components of liquid-crystalline mixtures. A further subject of the invention concerns liquid-crystalline mixtures containing at least one compound of the formula (I) and electrooptical display elements which contain such mixtures.

DETAILED DISCUSSION

In these novel compounds, the cyclohexyl rings are each in the trans-configuration, as indicated by dots in formula I.

At least one of the groups X and Y is a substituent having a polarizing action, from the group comprising fluorine, chlorine, bromine and cyano.

Particularly preferred are those compounds of the formula (I) in which one of the groups X and Y is fluorine, chlorine or cyano, in particular those in which X is fluorine and Y is hydrogen.

If r=1, the bridge member Z then present can be a single bond or a grouping selected from the groups of the formulae —CH$_2$CH$_2$—, —OCH$_2$—, —O—CO— or —CO—O—. Preferably, Z is —CH$_2$CH$_2$—, —OCH$_2$— or —O—CO—.

$R^1$ and $R^2$ are identical or different ring groups selected from C$_1$—C$_{12}$—alkyl and C$_1$—C$_{12}$—alkoxy groups having a straight or branched chain, which may be chiral, of the alkyl moiety, for example methyl, ethyl, propyl, butyl, pentyl, hexyl, heptyl, octyl, nonyl, decyl, undecyl or dodecyl as the alkyl moiety, including the corresponding chiral isomeric alkyl moieties, for example 1-methylpropyl, 1-methylbutyl, 2-methylbutyl, 1-methylpentyl, 2-methylpentyl, 3-methylpentyl, 1- or 2- or 3- or 4-methylhexyl, 1- or 2- or 3- or 4- or 5-methylheptyl and further alkyl-alkyl groups formed in accordance with this principle and having an asymmetrical carbon atom. Alkyl moieties having 2-8 carbon atoms, in particular 3-8 carbon atoms, are frequently preferred.

$R^1$ is preferably straight-chain alkyl having 2-8 carbon atoms. In the case of r=0, $R^2$ is preferably straight-chain alkoxy having 2-8 carbon atoms and, in the case of r=1, it is preferably straight-chain alkyl having 2-8 carbon atoms.

Preferred groups of compounds of the formula I according to the invention are of the following formulae Ia, Ib, Ic, Id, Ie, and If, in which $R^1$, $R^2$, X and Y have the meanings given above for formula I.:

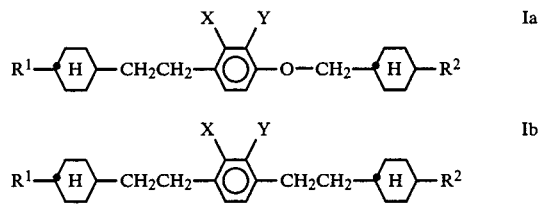

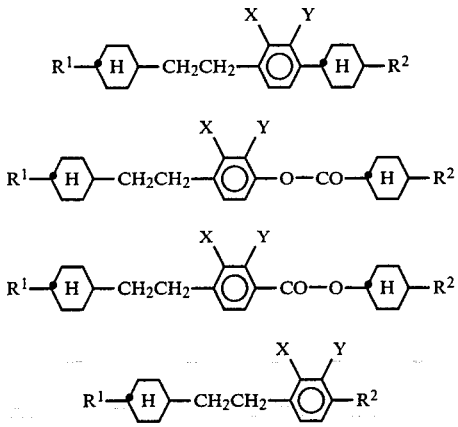

Those compounds of the formula If are preferred in which $R^2$ is alkoxy and $R^1$ is alkyl.

The novel compounds (I) can be prepared by various processes. A first general process is based on the condensation of a corresponding carboxylic acid derivative of the formula A—CH₂COOH, preferably in the form of the corresponding acid halide, in which A represents the left-hand part of the molecule of the compound (I), that is to say

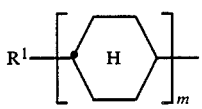

with a corresponding anisole derivative of the formula

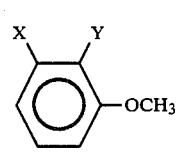

in order to form the corresponding ketone of the formula C

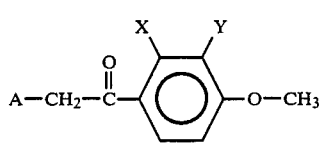

which is then reduced for replacing the ketocarbonyl oxygen by two hydrogen atoms, a compound of the formula

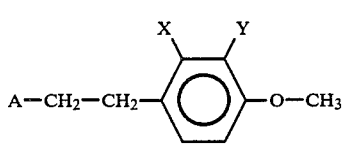

being formed.

For modifying $R^2$ or/and (if r=1) for introducing the structure E

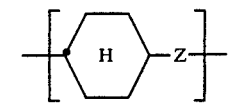

the compound D can be converted to a compound F

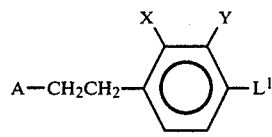

in which $L^1$ is a first reactive group, such as hydroxyl, COOH or halogen, and the compound F can then be reacted with a compound of the formula G

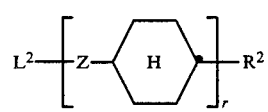

in which $L^2$ is a second reactive group, in order to form the target compound I or a pre-compound which can be converted into the latter.

Alternatively, the compounds I can also be prepared from appropriate pre-compounds of analogous structure, but without transversely polarizing substituents, by halogenation or transhalogenation and, if appropriate, nitrilation (replacement of halogen by cyano).

A specific example of the synthesis of preferred compounds I is illustrated by the equation which follows:

(1) reduction, for example with LiAlH₄

(2) bromination, for example with elementary bromine in acetonitrile (3) $CO_2$ Grignard (4) conversion into acid halide and reaction with 2-Y-3-X-anisole (5) reduction (6) demethylation, for example with boron tribromide (7) condensation with (trans-4-$R^2$-cyclohexyl)-methyl bromide The starting materials required for the various syntheses of the compounds I are either known or can be prepared by methods known per se from known starting materials.

The chemistry involved in the reactions described above is fully conventional per se and as applied to this invention. See, e.g., Houben-Weyl, Methoden der Organischen Chemie (Methods of Organic Chemistry), Georg-Thieme Verlag, Stuttgart; Organic Reactions, John Wiley & Sons, Inc., New York.

In the pure state, the compounds of the formula (I) are colorless and form liquid-crystalline mesophases in a temperature range favorable for electro-optical use. They are very stable chemically, thermally and towards light.

The compounds of the formula (I) have a wide range of application. Depending on the selection of the substituents, these compounds can be used as base materials, of which liquid-crystalline dielectrics are predominantly composed; however, liquid-crystalline base materials from other classes of compounds can also be added to compounds of the formula (I), for example in order to lower the dielectric and/or optical anisotropy of such a dielectric. The compounds of the formula (I) are also suitable as intermediates for the preparation of other substances, which can be used as constituents of liquid-crystalline dielectrics.

To prepare LC mixtures according to the invention, in each case at least one specific compound I is used as a component and is mixed, if appropriate, with other specific compounds I and/or with compounds known for the preparation of LC mixtures having a clearly negative DCA for use in GHD or HND systems. The compound I, of which there is at least one, here amounts as a rule to at least 5% by weight and, as a maximum, to 30% by weight of the LC mixture. If several compounds I are used, these can represent a predominant proportion, for example 50–90% by weight, of the mixture, with appropriate conventional selection. Preferably the LC mixtures contain 10–40% by weight of the compounds of formula I.

LC mixtures which virtually consist only of compound I are also included in the invention, up to 95–100% by weight.

One skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, M is the melting point and C is the clear point of a liquid crystal substance.

"Usual working-up" means: water is added, the mixture is extracted with methylene chloride, the phases are separated, the organic phase is dried and evaporated, and the product is purified by crystallization and/or chromatography. The phase transition temperatures quoted relate to degrees centigrade and are in each case given between the corresponding symbols of the phases "C" (crystalline), "N" (nematic), "I" (isotropic), "$S_A$" (A-smectic).

EXAMPLE 1

(a) Preparation of trans-4-pentylcyclohexylacetyl chloride.

For conversion into the acid chloride, trans-4-pentylcyclohexylacetic acid (12.0 g, 0.0566 mol) was reacted for about 1 hour on an oil bath at 80° C. with thionyl chloride (50 ml). The solution obtained was evaporated under reduced pressure, treated with absolute toluene (50 ml) and once more evaporated under reduced pressure.

(b) Preparation of 2-fluoro-4-methoxy-α-(trans-4-pentylcyclohexyl)-acetophenone

The acid chloride obtained according to section (a) was taken up in absolute dichloromethane (50 ml), without further purification, and added dropwise under virtually anhydrous conditions to a solution of 3-fluoroanisole (7.1 g, 0.0566 mol), aluminum chloride (8.3 g, 0.0623 mol) and absolute dichloromethane (100 ml). The mixture thus formed was stirred for 12 hours and then poured onto ice water which contained 50 ml of concentrated hydrochloric acid. The organic phase was separated off, and the aqueous phase was again extracted with dichloromethane (2×100 ml). The combined organic phases were then washed with water, sodium bicarbonate and water, and dried over magnesium sulfate. The crude product obtained after evaporation of the dichloromethane under reduced pressure was purified by recrystallization from hexane at 0° C. This gave 11.5 g (64% yield) of pure 2-fluoro-4-methoxy-α-(trans-4-pentylcyclohexyl)acetophenone, M. 71° to 72° C.

(c) Preparation of 2-(trans-4-pentylcyclohexyl)-1-(2-fluoro-4-methoxyphenyl)-ethane A mixture of the 2-fluoro-4-methoxy-α-(trans-4-pentylcyclohexyl)-acetophenone (10.0 g, 0.0313 mol) obtained according to section (b), aluminum lithium hydride (2.1 g, 0.0560 mol), aluminum chloride (15.0 g, 0.1125 mol), absolute ether (70 ml) and absolute chloroform (70 ml) was heated to gentle reflux for 5.5 hours under virtually anhydrous conditions.

The reaction solution was then cooled and subsequently treated with water-containing ether, water and concentrated hydrochloric acid. The aqueous phase was separated off and extracted twice more with ether (2×100 ml). The combined organic phases were then washed with water, sodium bicarbonate and water, dried over magnesium sulfate and then concentrated. The crude product was distilled in a bulb tube at 150° C./about $4 \times 10^{-2}$ mm Hg. This product (9.0 g, 94% yield) can be used for the following reaction without further purification.

(d) Preparation of 3-fluoro-4-[2-(trans-4-pentylcyclohexyl)-1-ethyl]-phenol

A solution of the 2-(trans-4-pentylcyclohexyl)-1-(2-fluoro-4-methoxyphenyl)-ethane (9.0 g, 0.0294 mol) obtained according to section (c) in absolute dichloromethane (100 ml) was added dropwise to a solution of boron tribromide (11.0 g, 0.0441 mol) and absolute dichloromethane (100 ml) under virtually anhydrous conditions at 0° C. The mixture thus formed was stirred for 1 hour and then poured onto ice water. The organic phase was separated off, and the aqueous phase was extracted again with dichloromethane (2×50 ml). The combined organic phases were washed with water and dried over magnesium sulfate. The crude product obtained after evaporation was recrystallized from hexane at 0° C. 8.5 g (98% yield) of pure target product were obtained.

(e) Preparation of 1-[2-(trans-4-pentylcyclohexyl)-1-ethyl]-4-(trans-4-propylcyclohexyl)-methoxy-2-fluorobenzene A mixture of the 3-fluoro-4-[2-(trans-4-pentylcyclohexyl)-1-ethyl]-phenol (2.0 g, 0.00068 mol) obtained according to section (d), (trans-4-propylcyclohexyl)-methyl bromide (2.0 g, 0.00089 mol), anhydrous potassium carbonate (3.8 g, 0.0274 mol) and absolute dimethylformamide (100 ml) was heated for 24 hours under reflux.

The reaction mixture was worked up as in section (d). The crude product was purified by column chromatography on silica gel with toluene as the eluant. After evaporation of the toluene, the product was recrystallized several times from ethanol, until the phase transition temperatures were constant; the corresponding values are as follows: C61.5.N110.I.

EXAMPLES 2 to 7

According to the process indicated in Example 1, and using the corresponding (trans-4-alkylcyclohexyl)-methyl bromides, the following compounds (I) according to the invention were prepared:
(Example)
(2) 1-[2-(trans-4-pentylcyclohexyl)-1-ethyl]-4-(trans-4-pentylcyclohexyl)-methoxy-2-fluorobenzene; C72.S$_A$73.N113.I;
(3) 1-[2-(trans-4-pentylcyclohexyl)-1-ethyl]-4-(trans-4-heptylcyclohexyl)-methoxy-2-fluorobenzene; C88.S$_A$94.N110.I;
(4) 1-[2-(trans-4-propylcyclohexyl)-1-ethyl]-4-(trans-4-propylcyclohexyl)-methoxy-2-fluorobenzene; C64.N108I;
(5) 1-[2-(trans-4-propylcyclohexyl)-1-ethyl]-4-(trans-4-pentylcyclohexyl)-methoxy-2-fluorobenzene; C54.5.N110.5.I;
(6) 1-[2-(trans-4-propylcyclohexyl)-1-ethyl]-4-(trans-4-heptylcyclohexyl)-methoxy-2-fluorobenzene; C72.5.S$_A$76.5.N107.5.I;
(7) 1-[2-(trans-4-heptylcyclohexyl)-1-ethyl]-4-(trans-4-propylcyclohexyl)-methoxy-2-fluorobenzene; C45.N108.I.

EXAMPLE 8

From 1-(4-trans-heptylcyclohexyl)-2-(3-fluoro-4-hydroxyphenyl)-ethane [M. 70°-71°; obtainable analogously to Example 1] and (trans-4-propylcyclohexyl)-methyl bromide, 1-[2-(trans-4-heptylcyclohexyl)-1-ethyl]-4-(trans-4-propylcyclohexyl)-methoxy-3-fluorobenzene is obtained analogously to Example 1; C50.5.S$_A$90.N110.I.

EXAMPLE 9

From 1-(4-trans-heptylcyclohexyl)-2-(3-bromo-4-hydroxyphenyl)-ethane [M. 50°-51°; obtainable by bromination of 1-(4-trans-heptylcyclohexyl)-2-(4-hydroxyphenyl)-ethane in dichloromethane], 1-[2-trans-4-heptylcyclohexyl)-1-ethyl]-4-(trans-4-propylcyclohexyl)-methoxy-3-bromobenzene is obtained analogously to Example 8; C44.N85.5.I.

EXAMPLE 10

From 1-(4-trans-4-heptylcyclohexyl)-2-(3-chloro-4-hydroxyphenyl)-ethane [M. 56°-57°, obtainable analogously to Example 1] and (trans-4-propylcyclohexyl)-methyl bromide, 1-[2-(trans-4-heptylcyclohexyl)-1-ethyl]-4-(trans-4-propylcyclohexyl)-methoxy-3-chlorobenzene is obtained analogously to Example 1; C46.N96.I.

EXAMPLE 11

From 1-(4-trans-4-heptylcyclohexyl)-2-(3-cyano-4-hydroxyphenyl)-ethane and (trans-4-propylcyclohexyl)methyl bromide, 1-[2-(trans-4-heptylcyclohexyl)-1-ethyl]-4-(trans-4-propylcyclohexyl)-methoxy-3-cyanobenzene is obtained analogously to Example 1; C57.S$_A$90.I.

EXAMPLE 12

A mixture of 1.0 g of 1-(4-trans-pentylcyclohexyl)-2-(2-fluoro-4-hydroxyphenyl)-ethane (Example 1), 0.8 g of 1-bromobutane, 1.9 g of potassium carbonate and 30 ml of butanone is boiled overnight. The reaction mixture is added to 250 ml of water, and this is extracted with three times 50 ml of chloroform. The combined organic phases are washed with twice 500 ml of water and dried over MgSO$_4$. Conventional working-up gives 1-(4-trans-pentylcyclohexyl)-2-(2-fluoro-4-butoxyphenyl)-ethane; C24.N26.I.

EXAMPLES 13 to 25:

Following the procedure indicated in Example 12, the following compounds I according to the invention were prepared, using the corresponding 1-(4-trans-alkylcyclohexyl)-2-(2-fluoro-4-hydroxyphenyl)-ethanes or the corresponding 1-(4-trans-alkylcyclohexyl)-2-(3-fluoro-4-hydroxyphenyl)-ethanes and the corresponding 1-bromoalkanes:
(Example)
(13) 1-(4-trans-propylcyclohexyl)-2-(2-fluoro-4-ethoxyphenyl)-ethane; M. 22°; C. 14° (monotropic);
(14) 1-(4-trans-propylcyclohexyl)-2-(2-fluoro-4-butoxyphenyl)-ethane; M. 21°; C. 12° (monotropic);
(15) 1-(4-trans-propylcyclohexyl)-2-(2-fluoro-4-hexyloxyphenyl)-ethane; M. 28°; C. 22° (monotropic);
(16) 1-(4-trans-pentylcyclohexyl)-2-(2-fluoro-4-ethoxyphenyl)-ethane; M. 32°; C. 28° (monotropic);
(17) 1-(4-trans-pentylcyclohexyl)-2-(2-fluoro-4-propoxyphenyl)-ethane; M. 22.5°; C. 10° (monotropic);
(18) 1-(4-trans-pentylcyclohexyl)-2-(2-fluoro-4-pentyloxyphenyl)-ethane; M. 26°; C. 12° (monotropic);
(19) 1-(4-trans-pentylcyclohexyl)-2-(2-fluoro-4-hexyloxyphenyl)-ethane; M. 23.5°; C. 29.5°;
(20) 1-(4-trans-heptylcyclohexyl)-2-(2-fluoro-4-ethoxyphenyl)-ethane; M. 46°; C 35° (monotropic);
(21) 1-(4-trans-heptylcyclohexyl)-2-(2-fluoro-4-butoxyphenyl)-ethane; M. 31°; C. 34°;
(22) 1-(4-trans-heptylcyclohexyl)-2-(2-fluoro-4-hexyloxyphenyl)-ethane; M. 29.5°; C. 35°;
(23) 1-(4-trans-heptylcyclohexyl)-2-(3-fluoro-4-methoxyphenyl)-ethane; M. 32°; C. 29° (monotropic);
(24) 1-(4-trans-heptylcyclohexyl)-3-(3-fluoro-4-ethoxyphenyl)-ethane; M. 53°; C. 34° (monotropic);
(25) 1-(4-trans-heptylcyclohexyl)-3-(3-fluoro-4-hexyloxyphenyl)-ethane; M. 45°; C. 35° (monotropic).

EXAMPLE 26

A mixture of 0.65 g of trans-4-pentylcyclohexane-carboxylic acid chloride and 10 ml toluene is added to a mixture of 0.9 g of 1-(trans-4-pentylcyclohexyl)-2-(2-fluoro-4-hydroxyphenyl)-ethane (Example 1), 2 ml of pyridine and 10 ml of toluene, and the whole is stirred overnight. The reaction mixture is poured into cold, dilute hydrochloric acid and worked up as usual. This gives 3-fluoro-4-[2-(trans-4-pentylcyclohexyl)-ethyl]-phenyltrans-4-pentylcyclohexane-carboxylate; M. 72.5°, C. 147°.

EXAMPLES 27 to 31

Following the procedure indicated in Example 26, the following compounds I according to the invention are prepared:
(27) '-fluoro-4-[2-(trans-4-propylcyclohexyl)-ethyl]-phenyl trans-4-propylcyclohexane-carboxylate; M. 72°; C. 140°;
(28) 3-fluoro-4-[2-(trans-4-propylcyclohexyl)-ethyl]-phenyl trans-4-pentylcyclohexane-carboxylate; M. 68°; C. 146.5°;
(29) 3-fluoro-4-[2-(trans-4-propylcyclohexyl)-ethyl]-phenyl trans-4-heptylcyclohexane-carboxylate; C. 84°.$S_A$91°.N140°.I;
(30) 3-fluoro-4-[2-(trans-4-pentycyclohexyl)-ethyl]-phenyl trans-4-propylcyclohexane-carboxylate; M. 65°; C. 141°;
(31) 3-fluoro-4-[2-(trans-4-pentylcyclohexyl)-ethyl]-phenyl trans-4-heptylcyclohexane-carboxylate; C. 100°.$S_A$111°.N142°.I.

The following are further examples of compounds of the formula I. They are prepared analogously to the foregoing.

2-(trans-4-pentyl-4'-bicyclohexyl)-1-(3-fluoro-4-pentylphenyl)-ethane;
2-(trans-4-pentyl-4'-bicyclohexyl)-1-(2-fluoro-4-pentyl-4'-bicyclohexyl)-1-(2-fluoro-4-pentylphenyl)-ethane;
2-(trans-4-pentyl-4'-bicyclohexyl)-1-(3-fluoro-4-butoxyphenyl)-ethane;
2-(trans-4-pentyl-4'-bicyclohexyl)-1-(2-fluoro-4butoxyphenyl)-ethane;
2-(trans-4-pentyl-4'-bicyclohexyl)-1-(3-cyano-4-pentylphenyl)-ethane;
2-(trans-4-pentyl-4'-bicyclohexyl)-1-(2-cyano-4-pentylphenyl)-ethane;
2-(trans-4-pentyl-4'-bicyclohexyl)-1-(3-cyano-4-ethoxypenyl)-ethane;
2-(trans-4-pentyl-4'-bicyclohexyl)-1-(3-cyano-4-butoxyphenyl)-ethane;
2-(trans-4-pentyl-4'-bicyclohexyl)-1-(3-cyano-4-hexyloxyphenyl)-ethane;
2-(trans-4-pentyl-4'-bicyclohexyl)-1-(2-cyano-4-ethoxyphenyl)-ethane;
2-(trans-4-pentyl-4'-bicyclohexyl)-1-(2-cyano-4-butoxyphenyl)-ethane;
2-(trans-4-pentyl-4'-bicyclohexyl)-1-(2-cyano-4-hexyloxyphenyl)-ethane;
2-fluoro-1-[2(trans-4-propylcyclohexyl)-1-ethyl]-4-[2-(trans-4-pentylcyclohexyl)-1-ethyl]-benzene;
3-fluoro-1-[2-(trans-4-propylcyclohexyl)-1-ethyl]-4-[2-(trans-4-pentylcyclohexyl)-1-ethyl]-benzene;
2-fluoro-1,4-di-[2-(trans-4-pentylcyclohexyl)-1-ethyl]-benzene;
2,3-difluoro-1,4-di-[2-(trans-4-propylcyclohexyl)-1-ethyl]-benzene;
2,3-difluoro-1,4-di-[2-(trans-4-pentylcyclohexyl)-1-ethyl]-benzene;
2,3-difluoro-1,4-di-[2-(trans-4-heptylcyclohexyl)-1-ethyl]-benzene;
2-cyano-1-[2-(trans-4-propylcyclohexyl)-1-ethyl]-4-[2-(trans-4-pentylcyclohexyl)-1-ethyl]-benzene;
3-cyano-1-[2-(trans-4-propylcyclohexyl)-1-ethyl]-4-[2-(trans-4-pentylcyclohexyl)-1-ethyl]-benzene;
2-cyano-1,4-di-[2-(trans-4-pentylcyclohexyl)-1-ethyl]-benzene;
2,3-dicyano-1,4-di-[2-(trans-4-propylcyclohexyl)-1-ethyl]-benzene;
2,3-dicyano-1,4-di-[2-(trans-4-pentylcyclohexyl)-1-ethyl]-benzene;
2,3-dicyano-1,4-di-[2-(trans-4-heptylcyclohexyl)-1-ethyl]-benzene.

The following examples relate to mixtures of compounds of formula I with other liquid-crystalline substances which can be used as dielectrics according to the invention.

EXAMPLE A

A liquid crystalline dielectric is prepared by mixing 0.25 g of 1-[2-trans-4-pentylcyclohexyl)-1-ethyl]-4-(trans-4-propylcyclohexyl)-methoxy-2-fluorobenzene (compound according to example 1) with 0.75 g of a known liquid crystalline phase consisting of 24.0% by weight of trans-1-(4-ethoxyphenyl)-4-propylcyclohexane, 21.2% of weight of trans-1-(4-butoxyphenyl)-4-propylcyclohexane, 19.3% by weight of trans,trans-4-butylcyclohexanecarboxylic acid-4'-(4-propylcyclohexyl)-phenylester and 35.5% by weight, of 4'-(trans-4-propyl-cyclohexyl)-benzoicacid-2'-cyano-4'-butyl phenylester. This mixture shows a DCA of −2.3.

EXAMPLE B

A liquid crystalline dielectric consisting of
15% by weight of trans-1-p-ethoxyphenyl-4-propylcyclohexane,
10% by weight of trans-1-p-butoxyphenyl-4-propylcyclohexane,
25% by weight of 4-ethyl-4'-(trans-4-pentylcyclohexyl)-biphenyl,
20% by weight of p-methoxybenzoic acid p-pentylphenylester and
30% by weight of 1-(4-trans-pentylcyclohexyl)-2-(2-fluoro-4-hexyloxyphenyl)-ethane
shows a negative DCA.

EXAMPLE C

A liquid crystalline dielectric consisting of
7% by weight of trans1-p-ethoxyphenyl-4-propylcyclohexane,
30% by weight of 4-ethyl-4'-(trans-4-pentylcyclohexyl)-2'-fluorbiphenyl,
9% by weight of 4-ethyl-4'-(trans-4-propylcyclohexyl)-biphenyl,
6% by weight of 4-ethyl-4'-(trans-4-pentylcyclohexyl)-biphenyl,
15% by weight of 4-(Trans-4-pentylcyclohexyl)-4'-(trans-4-propylcyclohexyl)-biphenyl,
23% by weight of p-m-methoxybenzoic acid p-pentylphenylester,
6% by weight of 3-fluoro-4-[2-(trans-4-pentylcyclohexyl)-ethyl]-phenyl-trans-4-pentylcyclohexane-carboxylate and
4% by weight of 2-(trans-4-pentyl-4'-bicyclohexyl)-1-(3-fluoro-4-pentylphenyl)-ethane shows a negative DCA.

EXAMPLE D

A liquid crystalline dielectric consisting of
- 13% by weight of r-1-cyano-cis-4-(trans-4-propylcyclohexyl)-1-pentylcyclohexane,
- 6% by weight of 2-p-cyanophenyl-5-propyl-1,3-dioxane,
- 9% by weight of 2-p-octyloxyphenyl-5-pentylpyrimidine,
- 7% by weight of 2-p-nonyloxyphenyl-5-hexylpyrimidine,
- 10% by weight of trans-4-propylcyclohexane carboxylic acid-p-ethoxyphenylester,
- 15% by weight of 4-(trans-4-pentylcyclohexyl)-4'-(trans-4-propylcyclohexyl)-biphenyl,
- 17% by weight of 1-(4-trans-pentylcyclohexyl)-2-(2-fluoro-4-hexyloxyphenyl)-ethane,
- 12% by weight of 1-(4-trans-pentylcyclohexyl)-2-(2-fluoro-4-ethoxyphenyl)-ethane and
- 11% by weight of 3-fluoro-4-[2-(trans-4-pentylcyclohexyl)-ethyl]-phenyl-trans-4-pentylcyclohexane-carboxylate shows a negative DCA.

EXAMPLE E

A liquid crystalline dielectric consisting of
- 27% by weight of 1-(4-trans-pentylcyclohexyl)-2-(2-fluoro-4-hexyloxyphenyl)-ethane,
- 11% by weight of 1-[2-(trans-4-propylcyclohexyl)-1-ethyl]-4-(trans-4-propylcyclohexyl)-methoxy-2-fluorobenzene,
- 39% by weight of 1-[2-(trans-4-heptylcyclohexyl)-1-ethyl]-4-(trans-4-propylcyclohexyl)-methoxy-2-fluorobenzene and
- 23% by weight of 1-(4-trans-pentylcyclohexyl)-2-(2-fluoro-4-butoxyphenyl)-ethane shows a negative DCA.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline dielectric comprising at least two liquid crystalline compounds, the improvement wherein at least one of these compounds is a nematic compound with a negative dielectric anisotropy of the formula

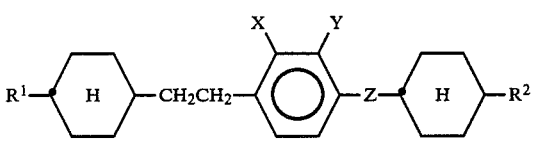

$R^1$ and $R^2$ are identical or different and each is alkyl of 1-12 carbon atoms,
Z is a bridging group which is —CH$_2$CH$_2$—, —OCH$_2$—, —O—CO— or —CO—O— and,
one of X and Y is flourine, chlorine, bromine or cyano and the other is hydrogen.

2. A compound of the formula

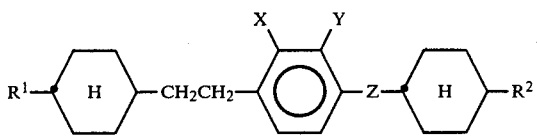

wherein
$R^1$ and $R^2$ are identical or different and each is alkyl of 1-12 carbon atoms,
Z is a bridging group which is —CH$_2$CH$_2$—, —OCH$_2$—, —O—CO— or —CO—O— and,
one of X and Y is fluorine, chlorine, bromine or cyano and the other is hydrogen.

3. A dielectric of claim 1, wherein $R^1$ or $R^2$ is straight chained.

4. A dielectric of claim 1, wherein $R^1$ or $R^2$ is a chiral branched group.

5. A dielectric of claim 1, wherein said nematic compound is of the formula

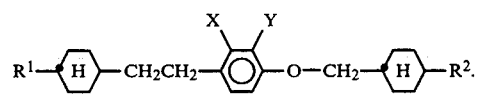

6. A dielectric of claim 1, wherein said nematic compound is of the formula

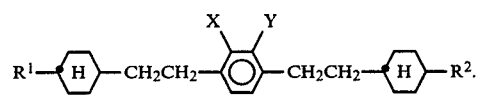

7. A dielectric of claim 1, wherein said nematic compound is of the formula

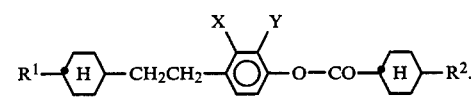

8. A dielectric of claim 1, wherein said nematic compound is of the formula

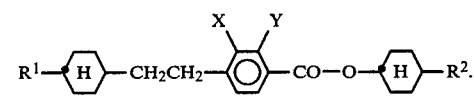

9. A dielectric of claim 1, wherein X is fluoro and Y is H.

10. A dielectric of claim 1, wherein Z is —CH$_2$CH$_2$—, —OCH$_2$— or —O—CO—.

11. A dielectric of claim 1, wherein $R^1$ is straight chain $C_{2-8}$-alkyl.

12. A compound of claim 2 of the formula

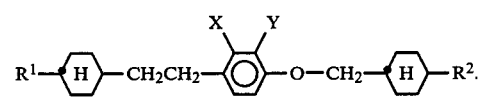

13. A compound of claim 2 of the formula

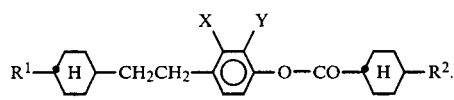

14. A compound of claim 2 of the formula

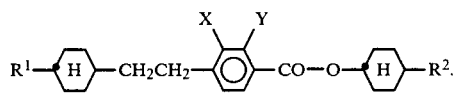

15. In an electro-optical display element comprising a liquid crystalline dielectric, the improvement wherein the dielectric is one of claim 1.

16. A electrooptical display element of claim 15 which is a guest/host display element or a homotropic-nematic display element.

17. A liquid crystalline dielectric of claim 7 wherein one of X and Y is F.

18. A liquid crystalline dielectric of claim 1 wherein one of X and Y is F.

19. A compound of claim 2 of the formula

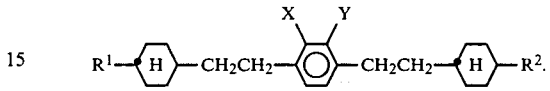

* * * * *